United States Patent [19]
Schefczik et al.

[11] Patent Number: 5,212,309
[45] Date of Patent: May 18, 1993

[54] 3-AMINOBENZENE-1,2,4,5-TETRACARBOXYLIC DIHYDRAZIDES AND COMPOSITION CAPABLE OF CHEMILUMINESCENCE, AND 3-AMINOBENZENE-1,2,4,5-TETRACARBOXYLIC DIANHYDRIDES

[75] Inventors: Ernst Schefczik, Ludwigshafen; Klaus Huemke, Friedelsheim, both of Fed. Rep. of Germany

[73] Assignee: BASF Aktiengesellschaft, Ludwigshafen, Fed. Rep. of Germany

[21] Appl. No.: 829,631

[22] Filed: Feb. 3, 1992

[30]     Foreign Application Priority Data

Feb. 5, 1991 [DE] Fed. Rep. of Germany ....... 4103405

[51] Int. Cl.$^5$ ................. C07D 487/04; C07D 493/04; C09K 11/07; C12Q 1/66
[52] U.S. Cl. ................................... 544/234; 252/700; 435/8; 436/98; 549/239
[58] Field of Search ................................. 544/234, 237

[56]     References Cited

U.S. PATENT DOCUMENTS

| | | | |
|---|---|---|---|
| 3,497,512 | 2/1970 | Hofer et al. | 544/237 |
| 4,226,992 | 10/1980 | Buckler et al. | 544/234 |
| 4,598,044 | 7/1986 | Kricka et al. | 544/234 |
| 4,665,181 | 5/1987 | Thomas et al. | 544/237 |

FOREIGN PATENT DOCUMENTS

| | | |
|---|---|---|
| 2924066 | 12/1980 | Fed. Rep. of Germany . |
| A419166 | 2/1967 | Switzerland . |
| 1100911 | 1/1968 | United Kingdom ................ 544/237 |

OTHER PUBLICATIONS

Gundermann Chemilumineszenz: Grundlagen-Beispiele-Mechanismen, Steinfatt, Praxis der Naturwissenschaften Chemie 37 (1988) 2-14.
Albrecht et al Chemie in unserer Zeit, 24 (1990) 227-238.
Hopff et al Chemical Abstract, 59, No. 2698 (1963).
Hopff et al Chemical Abstract, 55, No. 21043 (1961).
Hopff et al Chemical Abstract 55, No. 13363 (1961).

*Primary Examiner*—Robert T. Bond
*Assistant Examiner*—E. Bernhardt
*Attorney, Agent, or Firm*—Keil & Weinkauf

[57]     ABSTRACT

Chemiluminescenct 3-aminobenzene-1,2,4,5-tetracarboxylic dihydrazides.

3 Claims, No Drawings

3-AMINOBENZENE-1,2,4,5-TETRACARBOXYLIC DIHYDRAZIDES AND COMPOSITION CAPABLE OF CHEMILUMINESCENCE, AND 3-AMINOBENZENE-1,2,4,5-TETRACARBOXYLIC DIANHYDRIDES

The present invention relates to 3-aminobenzene-1,2,4,5-tetracarboxylic dihydrazides and to a composition capable of chemiluminescence, and to 3-aminobenzene-1,2,4,5-tetracarboxylic dianhydrides, and to processes for preparing the dihydrazides and dianhydrides.

Chemiluminescence (CL) is a well-defined part of the wide range of known manifestations of luminescence, in which the emission of light is causally connected with a particular chemical reaction.

The phenomenon itself is now known far beyond the restricted area of research facilities dealing scientifically with this topic. Chemical "cold light" is commercially available in the form of light sticks which are based on the chemical cleavage of oxalic esters.

Chemiluminescence has already made its entry into analytical laboratories via specifically constructed luminometers, especially in medical diagnosis. Thus, with electronic options now available, many substrates can be detected with an accuracy which was regarded only a few years ago as impossible to achieve. For example, ATP (adenosine triphosphate) can be detected down to the femtomole and attomole level with this method. Similar is true of Mg ions which are needed, in addition to oxygen and ATP, for light emission in the biochemical luciferin/luciferase system. It is even possible to determine calcium satisfactorily in the amounts which occur in a single cell in the body.

Examples of other compounds which can be detected by CL are fluorescent hydrocarbons and heterocycles, glucose in blood serum and various types of active oxygen as occur in organic and inorganic peroxides.

The three criteria determining the chemically generated luminescence are the chemical reaction, the energy conversion and the light emission, which depend on one another, and this shows that there is a close interrelation between physical and chemical contributions to the process.

The light energy is frequently emitted not in the visible but in the UV range. It is possible in this case, by adding true fluorophores, to convert the energy into visible light. Particularly suitable for this are extended aromatic systems with conjugated electron pairs, eg. 9,10-diphenylanthracene or 5,6,11,12-tetraphenyltetracene. However, the porphyrine system of the blood can also be used in this way. Usually employed for this purpose is the hemin from ox blood.

Oxygen has an essential importance in many light-generating processes. Bioluminescence is possible only when there is an oxygen supply. The autoxidation of hydrocarbons is likewise accompanied by light emission. The well-known glowing of white phosphorus is also CL, for which the reaction of PO with oxygen to give $PO_2$ is thought to be responsible. The reactions which lead to the appearance of CL are almost all oxidations.

A particularly well investigated class of substances is represented by the cyclodiacyl peroxides. These include phthaloyl peroxide, which produces brilliant CL with a number of fluorophores.

The CL of the dioxetanes and derivatives thereof is well known and particularly thoroughly investigated because of its high quantum yield.

The perhydrolysis of various oxalic acid derivatives, which takes place with intense CL, is currently the best of the known CL systems in terms of quantum yield (up to 0.34 einstein/mol) and utilizability as chemical light source. It takes place via oxidative formation of dioxetanes as intermediate and various rearrangements until excited carbon dioxide is formed.

The mechanism of the chemiluminescence of 3-aminophthalhydrazide is one stage more complicated. 3-Aminophthalhydrazide forms, via a diazaquinone intermediate and further reaction steps, an intramolecular dioxirane/carbene system which is highly fluorescent and emits its energy as intense blue fluorescence during an intramolecular carbene oxidation which results in the dianion of 3-aminophthalic acid.

One of the best investigated bioluminescences is the luciferin/luciferase system of the American firefly, which resembles the glow worm. It is used in medical diagnosis for determination of ATP and Mg.

However, the difficulty associated with using this reaction is that the enzyme luciferase is needed for it.

Recent developments have centered more on analysis and diagnosis than on illumination.

A review of the prior art is to be found in the article by M. Steinfatt, "Chemilumineszenz: Grundlagen-Beispiele-Mechanismen", Praxis der Naturwissenschaften-Chemie 37 (1988) 2–14, which also points out the need to improve available CL systems.

It is an object of the present invention to provide effective compounds which are, where possible, easily obtainable and which, in particular, have excellent chemiluminescence properties for use in analysis.

We have found that this object is achieved by 3-aminobenzene-1,2,4,5-tetracarboxylic dihydrazides of the following formula I

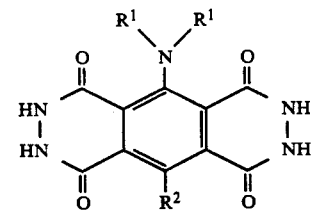

where $R^1$ is H, methyl or ethyl and $R^2$ is H, $C_{1-6}$-alkyl or $C_{1-6}$-alkoxys.

An electron-releasing substituent (+I and/or +M effect) in position 6 proves beneficial.

A particularly suitable representative is, for example, 3-amino-6-methylbenzene-1,2,4,5-tetracarboxylic dihydrazide.

The 3-aminobenzene-1,2,4,5-tetracarboxylic dihydrazides can also be called 3-aminopyromellitic dihydrazides.

They are prepared, for example, by a relatively straightforward chemical reaction from 3-aminobenzene-1,2,4,5-tetracarboxylic dianhydrides with hydrazine hydrate in, for example, ethanolic solution.

The reaction takes place as shown in the following scheme:

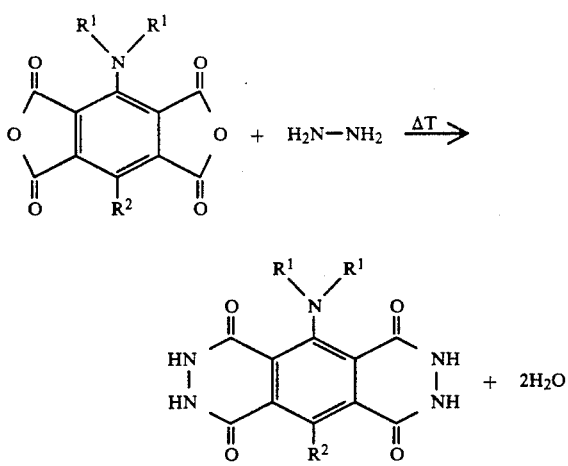

where $R^1$ and $R^2$ have the abovementioned meanings.

The dianhydrides of the formula II

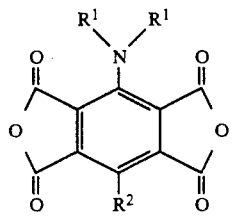

II where $R^1$ is H, methyl or ethyl and $R^2$ is H, $C_{1-6}$-alkyl or $C_{1-6}$-alkoxy, are intermediates in the preparation of the dihydrazides of the formula I according to the invention. They are prepared from substituted anilines of the formula III

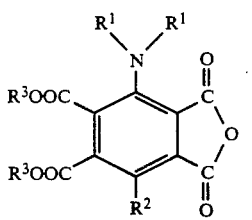

III where $R^1$ and $R^2$ have the abovementioned meanings, and $R^3$ is identical or different $C_1$-$C_8$-alkyl, by heating the substituted anilines in the presence of acids, which gives the dianhydrides directly. The dianhydrides can, however, also be obtained from the substituted anilines by stepwise reaction, ie. with intermediate isolation of the carboxylic acids. The preparation of the substituted anilines is described in DE 29 24 066 A1.

We have also found that chemiluminescence occurs on oxidation of the dihydrazides according to the invention with hydrogen peroxide in alkaline solution.

The present invention therefore also relates to a composition capable of chemiluminescence, especially in analysis, containing substances of the above formula I.

EXAMPLES

Preparation Example

Preparation of 3-amino-6-methylbenzene-1,2,4,5-tetracarboxylic dianhydride 500 parts of 70 % strength sulfuric acid are stirred at 120° C while 293 parts of 3-methyl-4,5-bis-(methoxycarbonyl)-6-aminophthalic anhydride are added a little at a time. The mixture is stirred at 125° C. for 4 hours, allowed to cool and poured into 500 parts of ice. The product is filtered off with suction and washed with ice-water until free of sulfuric acid, and is dried at 120° C.

Yield: 210 parts of 3-amino-6-methylpyromellitic dianhydride in the form of a yellow crystalline powder. The compound can be recrystallized from acetic acid and does not melt up to 350° C. Elemental analysis gave the following results:

$C_{11}H_5NO_6$ (247) %
calculated: C 53.5, H 2.0, N 5.7, O 38.9,
found: C 53.3, H 2.2, N5.7, O 38.8.

Similar results are obtained when the 70 % strength sulfuric acid is replaced by the same amount of 50 %, 60 % or 80 % strength sulfuric acid.

1. Preparation of 3-amino-6-methylbenzene-1,2,4,5-tetracarboxylic dihydrazide 20.0 g (0.081 mol) of 3-amino-6-methylbenzene-1,2,4,5-tetracarboxylic dianhydride are dissolved in 200 ml of ethanol by refluxing in a 500 ml flask with stirrer, reflux condenser and internal thermometer. The solution is filtered hot and then cooled. At room temperature, 50.0 g (0.74 mol) of hydrazine hydrate (about 100 % pure) are added dropwise over the course of 10 minutes. An initial yellow precipitate dissolves on further addition. The reaction is slightly exothermic, and once this has subsided the mixture is refluxed for 2 to 3 hours to give a finely divided reddish brown precipitate. After standing overnight, the precipitate is filtered off with suction and thoroughly washed with cold ethanol.

Appropriate safety measures should be taken because of the toxicity (carcinogenicity) of the excess hydrazine hydrate.

The substance is dried at 50° C. under reduced pressure and recrystallized from aqueous ethanol as monohydrate.

Yield: 26.0 g (92.5 % of theory)
Melting point: >320° C.
Elemental analysis

| Elemental analysis: | C | H | N | O |
| --- | --- | --- | --- | --- |
| [%] theor.: | 45.1 | 4.0 | 27.6 | 23.3 |
| found: | 44.7 | 4.4 | 28.0 | 22.9 |

IR (KBr): 3334 (m); 1711 (s); 1625 (m); 1415 (m); 1242 (m); 1106 (w); 705 (w) cm.. H-NMR (DMSO): 2.31 (s); 2.51 (s); 2.74 (s); 2.93 (s); 4.46 (d); 6.05 ... 7.85 (m).

2. Generation of Chemiluminescence by Oxidation With peroxide in alkaline solution Reagents and volumetric solutions required:
a) 1/10,000 molar solution of 3-amino-6-methylbenzene-1,2,4,5-tetracarboxylic dihydrazide in deionized water b) 1/100 molar aqueous potassium hydroxide solution
c) 1 % strength aqueous hydrogen peroxide solution
d) 1/10,000 molar aqueous hemin solution (from ox blood)
e) 1/1000 molar alcoholic solution of 9,10-diphenylanthracene
f) 1/10,000 molar aqueous solution of 3-aminophthalhydrazide (luminol)

Test 1

3 ml of b) are added to 10 ml of a). 2 ml of d) are added and then 2 ml of c). An intense blue-violet light can be seen in a room with subdued lighting. The intensity decreases with time. However, the illumination is still detectable 10 minutes after the start of the reaction.

Test 2:

3 ml of b) are added to 10 ml of a). 2 ml of e) are added, and then 2 ml of c). An intense blue illumination can be seen in a room with subdued lighting, and its intensity decreases with time. A pale blue glow is still detectable 10 minutes after the start of the reaction.

Comparison:

3 ml of d) are added to 10 ml of f). 2 ml of d) are added, and then 2 ml of c). A pale blue illumination can be seen in a darkened room, but this rapidly loses intensity and is no longer visible after about 5 minutes.

It is evident from these tests that the substances according to the invention have distinctly better CL properties than the known 3-aminophthalhydrazide.

The substance according to the invention can be incorporated in a conventional manner into or onto a protein via the amino group in position 3 ($R^1=H$). Subsequent oxidation with peroxides in alkaline solution results in emission of light which can be utilized in biochemical and medical analysis, in particular for determining ATP and Ca or Mg ions. A description of uses of these types in clinical chemistry, biochemistry and medicine is to be found in "Chemie in unserer Zeit", 24 (1990) 227–238, to which reference is made.

We claim:

1. A 3-aminobenzene-1,2,4,5-tetracarboxylic dihydrazide of the following formula I

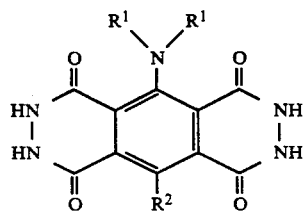

where $R^1$ is H, methyl or ethyl and $R^2$ is H, $C_{1-6}$-alkyl or $C_{1-6}$-alkoxy.

2. A substance of the formula I as claimed in claim 1, where $R^1$ is H and $R^2$ is $C_{1-3}$-alkyl.

3. 3-Amino-6-methylbenzne-1,2,4,5-tetracarboxylic dihydrazide.

* * * * *